(12) United States Patent
Dees et al.

(10) Patent No.: US 9,204,884 B2
(45) Date of Patent: Dec. 8, 2015

(54) DEVICE AND METHOD FOR DISTAL RESECTIONS OF A KNEE PROSTHETIC

(75) Inventors: Roger Ryan Dees, Senatobia, MS (US); Jason Sean Jordan, Hernando, MS (US)

(73) Assignee: Smith & Nephew, Inc., Memphis, TN (US)

(*) Notice: Subject to any disclaimer, the term of this patent is extended or adjusted under 35 U.S.C. 154(b) by 1390 days.

(21) Appl. No.: 12/444,363

(22) PCT Filed: Oct. 4, 2007

(86) PCT No.: PCT/US2007/080450
§ 371 (c)(1),
(2), (4) Date: May 15, 2009

(87) PCT Pub. No.: WO2008/043021
PCT Pub. Date: Apr. 10, 2008

(65) Prior Publication Data
US 2010/0094301 A1 Apr. 15, 2010

Related U.S. Application Data

(60) Provisional application No. 60/828,158, filed on Oct. 4, 2006.

(51) Int. Cl.
*A61B 17/58* (2006.01)
*A61B 17/15* (2006.01)
*A61B 17/17* (2006.01)

(52) U.S. Cl.
CPC ........... *A61B 17/155* (2013.01); *A61B 17/1764* (2013.01)

(58) Field of Classification Search
CPC ....................................... A61B 17/58
USPC .......................................... 606/89
See application file for complete search history.

(56) References Cited

PUBLICATIONS

European Patent Office, First Office Action, dated Feb. 11, 2015, 4 pages.
Japanese Patent Office, Decision of Rejection, dated Mar. 2, 2015, 4 pages.

*Primary Examiner* — Thomas J Sweet
*Assistant Examiner* — Matthew Schall
(74) *Attorney, Agent, or Firm* — David A. Chambers

(57) ABSTRACT

A device and method for resecting a distal portion of a femur comprises a distal cutting guide [98], a valgus guide [102], and a variable collet [10]. The distal cutting guide [98] is configured to overlie an anterior portion of the femur and comprises a slot for guiding a cutting tool across a distal portion of the femur. The valgus guide [102] is configured to connect to the distal cutting guide [98]. The valgus guide [102] is configured to align the slot of the distal cutting guide [98] at the proper varus/valgus angle. The variable collet [10] is configured to attach to an intramedullary rod and the valgus guide [102]. The variable collet [10] comprises a port [30] for receiving the intramedullary rod. The port [30] is angularly adjustable with respect to the valgus guide [102] such that adjusting the port [30] adjusts the varus/valgus angle of the distal cutting guide [98].

10 Claims, 12 Drawing Sheets

DEVICE AND METHOD FOR DISTAL RESECTIONS OF A KNEE PROSTHETIC

CROSS-REFERENCE TO RELATED APPLICATIONS

This application is a U.S. National Phase filing of International Application No. PCT/US2007/080450 which claims priority to U.S. Provisional Patent Application 60/828,156 filed Oct. 4, 2006, titled "Variable Transition Referencing Guide". The applications are herein incorporated by reference.

BACKGROUND OF THE INVENTION

1. Field of the Invention

This invention relates generally to cutting guides and blocks for bone preparation of a femur and, more particularly, distal cutting guides for preparation of the distal portion of the femur.

2. Related Art

In preparing the knee for implantation of a prosthesis in knee replacement surgery (either total knee replacement or partial knee replacement), the distal femur requires cuts on the bone in precise locations and precise planar angles. In many instances, the first cut may be a distal cut on the femur. Further cuts, including anterior, posterior, and any intermediate angled cuts, may be referenced from the distal cut. Thus, the distal cut may be used to orient all other cuts on the distal portion of the knee. Properly aligning the distal cutting block prior to making the distal cut may create a better fit and better performance of knee prosthesis.

Fixation of the cutting block to the femur has been accomplished by intramedullary (IM) rods or by pinning the guide to the femur. The IM rod may also be used as an alignment guide to orient a distal cutting guide. However, a surgeon does not align the cutting block perpendicular to the IM canal (the anatomical axis of the femur). Instead, the surgeon may align to a default angular offset that is built in to the cutting guide and is fixed within the cutting guide. Thus, if the surgeon desires to adjust the angle between the IM canal and the cutting guide (which affects the varus/valgus angle between the femur and tibia) then a different cutting block may be required having a different fixed cutting guide orientation. Additional cutting guide orientations require those blocks to be sterilized and present in the operating room at the time of surgery. This increases the possibility of error and may increase operating room time.

Other cutting blocks may include variability in the cutting guides relative to the pinned portions of the cutting block, but these cutting guides generally offset the plane of the cutting guides relative to the cutting blocks. Such changes may affect the amount of the resection and result in improper installation and performance.

Thus, there remains a need in the art for an easily adjustable distal cutting block for locating distal cutting guides for proper angle and depth of the distal resection.

SUMMARY OF THE INVENTION

It is in view of the above problems that the present invention was developed. A device and method for resecting a distal portion of a femur may comprise a distal cutting guide, a valgus guide, and a variable collet. The distal cutting guide is configured to overlie an anterior portion of the femur and comprises a slot for guiding a cutting tool across a distal portion of the femur. The valgus guide is configured to connect to the distal cutting guide. The valgus guide is configured to align the slot of the distal cutting guide at the proper varus/valgus angle. The variable collet is configured to attach to an intramedullary rod and the valgus guide. The variable collet comprises a port for receiving the intramedullary rod. The port is angularly adjustable with respect to the valgus guide such that adjusting the port adjusts the varus/valgus angle of the distal cutting guide.

Another embodiment comprises a locking portion configured to fix the variable collet to the intramedullary rod.

Yet another embodiment comprises a depth gage configured to adjust the depth of the distal cutting guide relative to the femur.

Alternatively, the depth gage may be further configured to fix the distal cutting guide to the valgus guide.

Another embodiment of the distal cutting guide includes a unicondylar distal cutting guide.

In yet another embodiment, the port has a first end and a second end, the first end configured to receive an end cap and the second end configured with a spherical surface, the spherical surface being a bearing surface configured to rotate the port within the collet.

Another embodiment further comprises a tensioner portion configured to tension the port such that the tension is generated from a force exerted oppositely on the spherical surface and the end cap.

Yet another embodiment further comprises a bias member configured to bias the tensioner portion.

Alternatively another embodiment of the valgus guide is fixed at an angle other than a perpendicular angle to the variable collet thereby aligning the slot of the distal cutting guide at a nonperpendicular angle to the anatomical axis of the femur.

Another embodiment further comprises indicia on the collet at the port to adjustably align the varus/valgus angle of the distal cutting guide.

A method of resecting a distal portion of a femur may comprise driving an intramedullary rod in the intramedullary canal of the femur. Another step may align a slot over an anterior portion of the femur. A step attaches a guide to the intramedullary rod. Another step attaches the slot to the guide. The slot is angularly adjustable with respect to the guide such that adjusting the guide adjusts the varus/valgus angle of the slot.

Another embodiment further comprises the step of locking the guide to the intramedullary rod.

Yet another embodiment further comprises the step of adjusting the depth of the slot relative to the femur.

An embodiment further comprises the step of fixing the slot to the guide.

Alternatively, the slot guides a unicondylar distal cutting tool.

In another embodiment, the method step of attaching the slot to the guide step further comprises rotating the guide relative to a bearing surface to adjust the varus/valgus angle of the slot with respect to the guide.

In yet another embodiment, the method step of locking further comprises the step of tensioning the guide such that the guide is fixed to the intramedullary rod.

In another embodiment, the method further comprises the step of biasing the guide in tension such that a force is required generally along the axis of the intramedullary rod to tension the guide.

Alternatively, the guide is fixed at an angle other than a perpendicular angle to the intramedullary rod thereby aligning the slot at a nonperpendicular angle to the anatomical axis of the femur.

Another embodiment further comprises the step of indicating the varus/valgus angle of the guide.

The invention has several advantages over prior devices and techniques which may be addressed by some of the embodiments. First, the number of necessary cutting blocks may be limited. Second, accurate placement, which may lead to better performance of the knee prosthesis is allowed from the ability to adjust the varus/valgus angle. Other advantages of the embodiments may also be apparent from the type of cutting block used.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

DETAILED DESCRIPTION OF THE EMBODIMENTS

Figure 1:
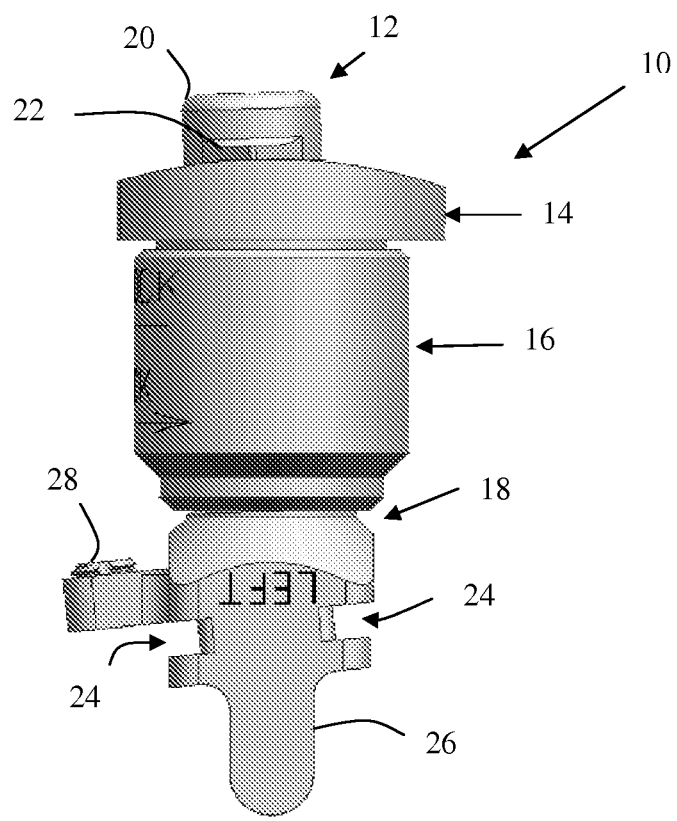
FIG. 1 is an embodiment of a variable collet.

Referring to the accompanying drawings in which like reference numbers indicate like elements, FIG. 1 is an embodiment of a variable collet 10. The variable collet 10 includes an IM rod guide 12, an upper tensioner portion 14, a lower locking portion 16 and a distal cutting frame 18. The IM rod guide 12 includes a tensioner cap 20 and a varus/valgus indicator 22. The distal cutting guide frame 18 includes distal block assembly receiving slots 24, intracondylar guides 26 and a set screw 28. The collet 10 is configured to slide over an IM rod to position a distal cutting block in the proper orientation. The IM rod guide 12 orients the angle between the IM rod and the distal cutting block. The locking portion locks the angle in place. The distal cutting frame 18 sets the plane for the distal cutting guide.

The distal cutting block (examples of which are shown in FIGS. 9-12) is oriented in a plane defined by the receiving slots 24. The receiving slots are fixed with respect to the locking portion 16. The receiving slots 24 may be perpendicular to the locking portion 16 or may be placed at an angle to the locking portion 16. The angular offset may be set to align the distal cutting block along the mechanical axis of the femur. The varus/valgus indicator 22 may indicate the angle either relative to the offset, or relative to the actual varus/valgus angle.

In FIG. 1, the embodiment is offset 6 degrees from perpendicular. Changing the angle of the IM rod guide 12, then, rotates the varus/valgus angle from the 6 degree offset value built into the collet 10. While the embodiment shown is at 6 degrees, any choice of offset may be given. Changing the offset may be beneficial based upon the population of likely surgical candidates. The minimum and maximum varus/valgus angle is determined from the amount of rotation the IM rod guide 12 can achieve in the collet 10. The range of angles from the offset may be equally spaced from the offset, for example, by setting the offset at an expected average for a population, then variation from the average, assuming a normal distribution, would allow for most of the population to be easily adjustable from the average. If, however, the population has a skewed distribution, then the average may not be best accounted for by offsetting the angle so that the range encompasses as many possible members of the population as possible. Instead, the skew may dictate setting the angle closer to the longer tail of the distribution to allow for the variable collet 10 to be used on as many people as possible.

Once the angle is set, then the locking portion 16 is rotated to lock the IM rod guide 12 in place. The locking portion 16 rotates relative to the tensioner portion 14. The tensioner portion 14 extends from the locking portion 16. The tensioner portion 14 presses against the tensioner cap 20 and the varus/valgus indicator 22 to lock the IM rod guide 12. The tensioner portion 14 may be any device that puts tension on the IM rod guide 12 to lock the IM rod guide 12 in place with respect to the receiving slots 24.

The distal cutting guide frame 18 sets the depth and orientation of the cutting guide. The depth is set by the intracondylar guides 26. The guides 26 position the receiving slots 24 above the intracondylar notch. The collet 10 slides down the IM rod until the intracondylar guides 26 rest in the notch. The receiving slots set the angle of the distal block relative to the IM rod. The set screw 28 may be used to fix the cutting block to the frame 18.

Figure 2:
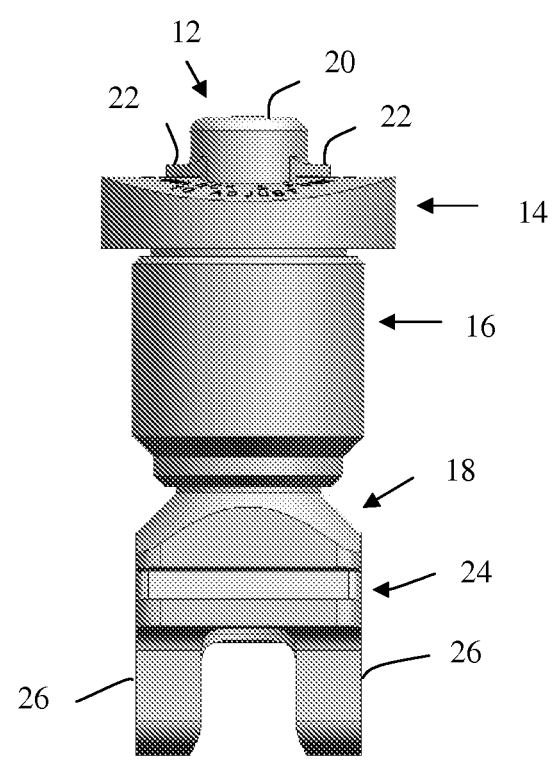
FIG. 2 is a side view of the variable collet of FIG. 1.

Turning now to FIG. 2, FIG. 2 is a side view of the variable collet 10 of FIG. 1. The collet 10 shows the intracondylar guides 26 are displaced anteriorly and posteriorly from the center of the collet 10. The indicators 22 also may be located on both anteriorly and posteriorly (A/P plane). The cutting block guides 24 are also oriented in the A/P plane so that the distal cutting block does not rotate in the A/P direction. The other portions of the collet 10, including the locking portion 16, the IM rod guide 20 and the upper tensioner 14 are generally cylindrical so that rotation may be achieved with the surgeon's fingers. However other shapes may be used for ease of use, such as hexagonal cross sections (like a bolt).

The upper face of the tensioner portion 14 may be rounded. The surface may be rounded to accommodate the rotation of the IM rod guide 12. The arc of the surface may be an arc having a radius the length of the IM rod member. This allows for the IM rod member to rotate without having to change the tension in the tensioner portion 14.

Figure 3:
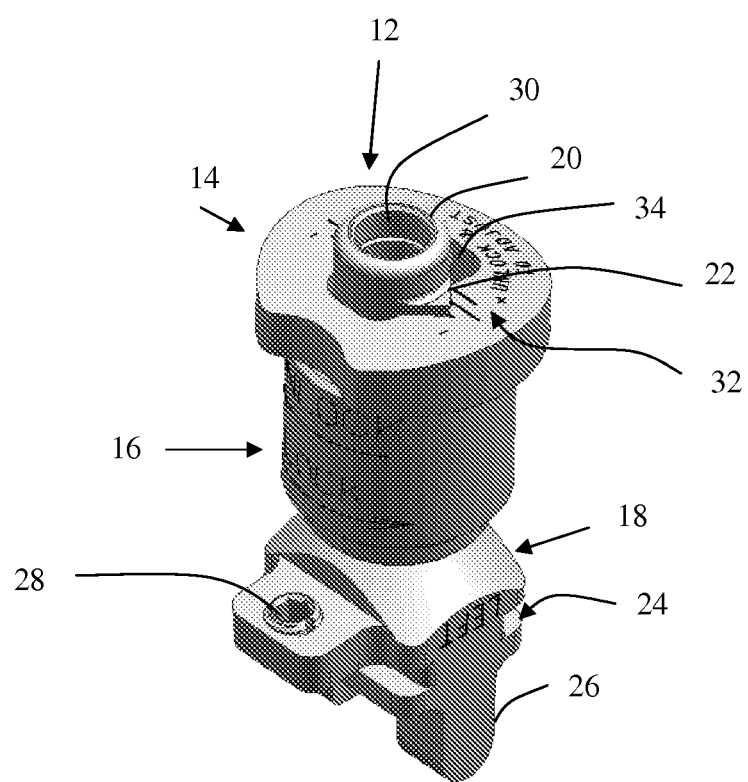
FIG. 3 is another view of the variable collet of FIG. 1.

Turning now to FIG. 3, FIG. 3 is another view of the variable collet 10 of FIG. 1. The IM rod guide 12 includes an IM rod port 30 and varus/valgus indicia 32. The IM rod port 30 receives an IM rod. The port 30 extends fully through the collet 10, passing through the locking portion 16 and the cutting guide frame 18. The indicia 32 may display numerical values for varus/valgus angle or may set a plus/minus from the offset. The indicia 32 may include indices for any number of possible settings. The example shown has an index for the offset, one for a more varus orientation, and one for a more valgus orientation. While there are only three indices, the amount of variation is not limited to only those three positions. The collet 10 may be set to any value within the range from varus to valgus angles rotatable in the collet 10.

The angular range of the collet 10 is controlled by a tensioner slot 34. The tensioner slot 34 sets the range of motion of the IM rod guide 12 in the medial-lateral direction. The walls of the tensioner slot 34 limit the motion.

The set screw 28 is threaded into the distal cutting guide frame 18. The set screw may be a hex head screw which may be tightened onto the cutting block assembly to hold the assembly rigid to the collet 10. An indention on the tensioner 14 may allow for clearance of a tool to set the set screw 28. Other tightening mechanisms (like a thumb wheel, a cam, etc.) may be used instead of the hex head set screw 28.

Figure 4:
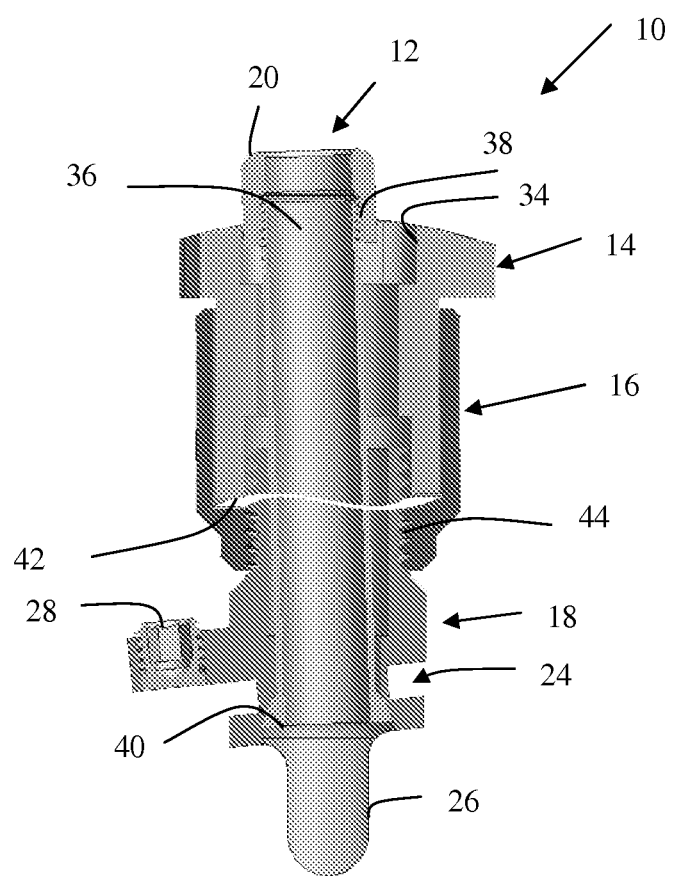
FIG. 4 is a cutaway of the variable collet of FIG. 1.

Turning now to FIG. 4, FIG. 4 is a cutaway of the variable collet of FIG. 1. The IM rod guide 12 includes an IM rod tube 36 and a wave spring 42. At one end, the IM rod tube 36 has a threaded tube portion 38 which threads into the tensioner cap 20. At the other end, a spherical end portion 40 is the rotating surface between the tube 36 and the frame 18. The frame 18 also includes a threaded frame portion 44 which threads into the locking portion 16. The wave spring 42 is positioned between the locking portion 16 and the tensioner portion 14. The wave spring 42 biases the tensioner portion 14. Other connections may be used to exert force from the locking portion 16 to the tensioner portion 14.

The tensioner cap 20 is pressed against the tensioner portion 14 by rotating the locking portion 16. The locking portion 16 rotates on the threaded portion 44 upward to press against the wave spring 42. The wave spring biases and pushes the tensioner portion 14 against the tensioner cap 20. When the tensioner portion 14 presses against the tensioner cap 20, the IM rod tube 36 is tensioned between the interface at the tensioner cap 20 and tensioner portion 14 and the interface between the spherical end portion 40 and the cutting guide frame 18.

Figure 5:
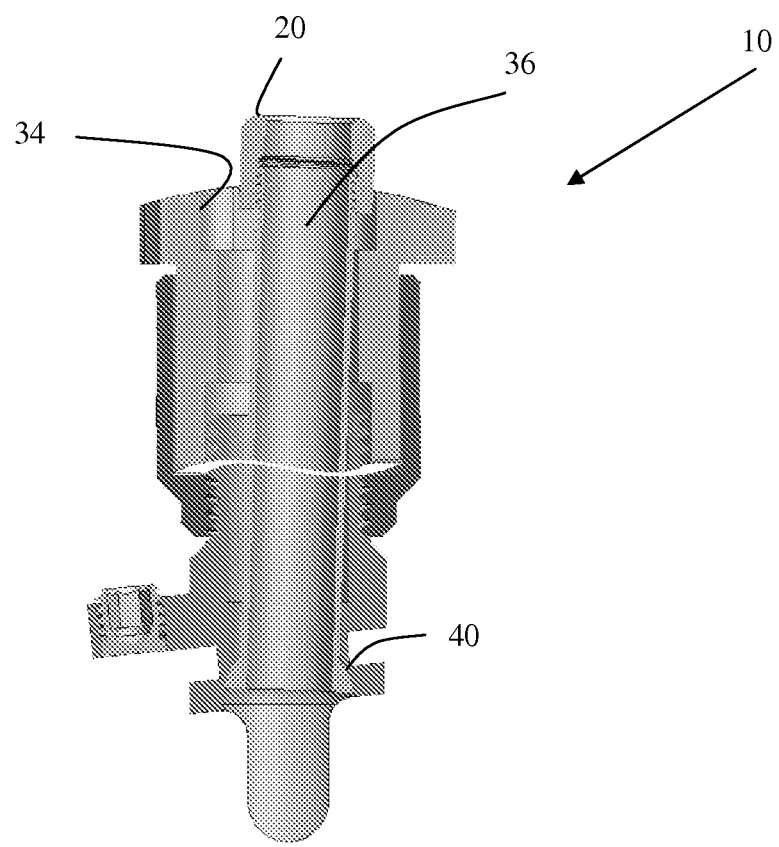
FIG. 5 is a cutaway of the variable collet of FIG. 1 showing a separate orientation of the collet.

In FIG. 4, the IM rod tube is fully rotated to the left (corresponding to the negative orientation from the indicia shown in FIG. 2. In contrast, turning now to FIG. 5, FIG. 5 is a cutaway of the variable collet 10 of FIG. 1 showing a separate orientation of the collet 10. The IM tube rod 36 is fully rotated to the right (corresponding to the positive orientation from the indicia shown in FIG. 2. The tensioner cap 20 abuts the tensioner slot 34 on the left side of the slot 34. The spherical end portion 40 allows for the tube 36 to be rotated while maintaining contact with the frame 18.

Figure 6:
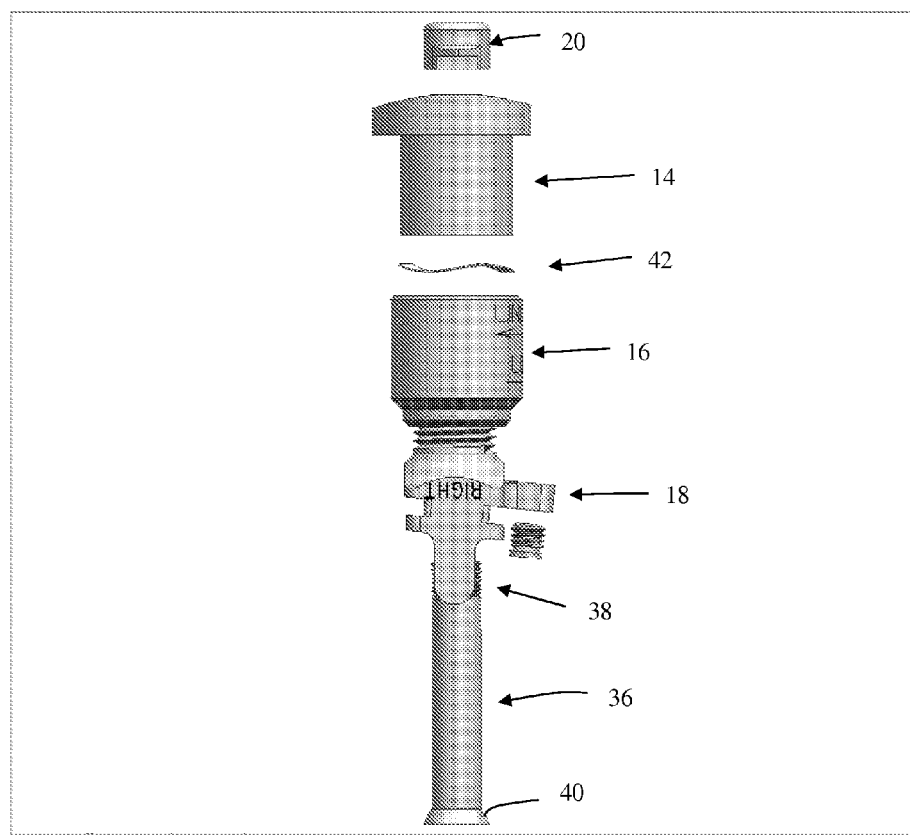
FIG. 6 is an exploded view of the variable collet of FIG. 1.

Turning now to FIG. 6, FIG. 6 is an exploded view of the variable collet 10 of FIG. 1. The tube 36 is inserted from below through the frame 18. The locking portion 16 is threaded onto the frame 18. The spring 42 and tensioner portion 14 are placed within the locking portion 16. The tensioner portion 14 is free to rotate within the locking portion 16. The tensioner cap 20 is threaded onto the threaded tube portion 38 to connect all portions of the collet 10 between the spherical end portion 40 and the tensioner cap 20.

Figure 7:
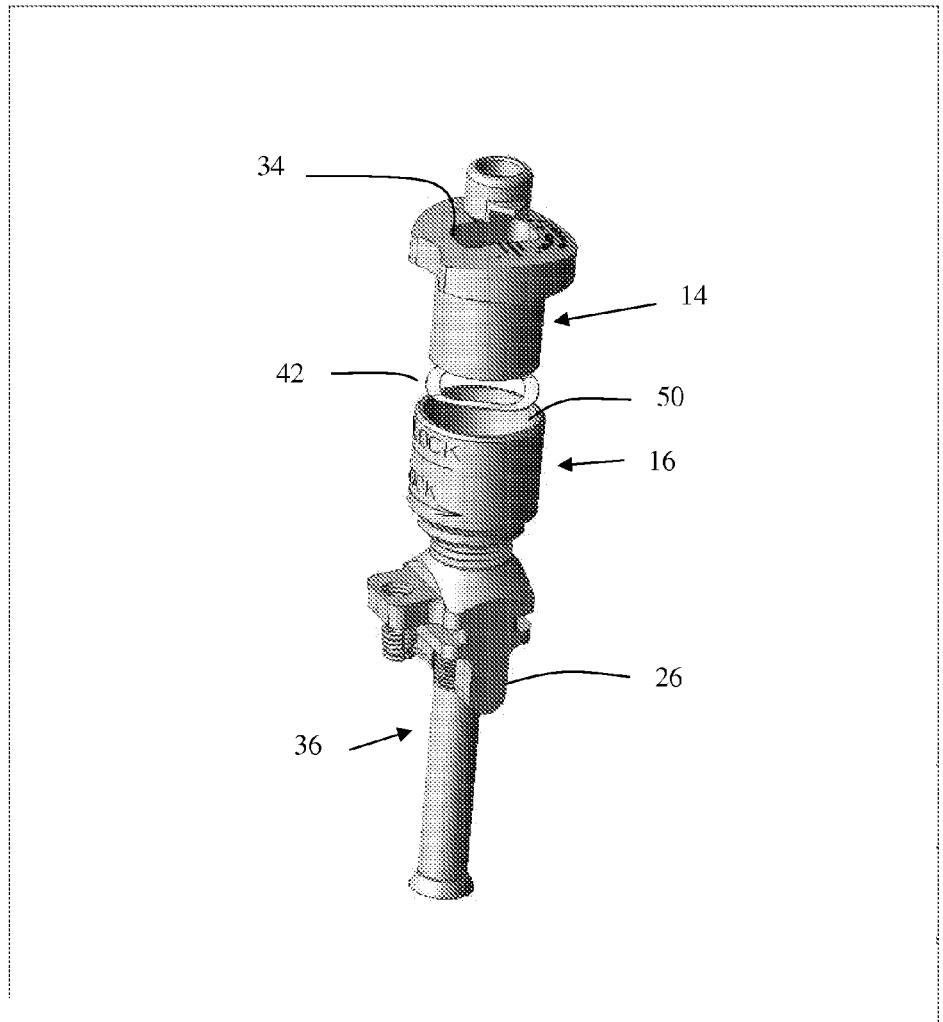
FIG. 7 is another exploded view of FIG. 6.

Turning now to FIG. 7, FIG. 7 is another exploded view of FIG. 6. The locking portion 16 includes a cavity 50 to receive the wave spring 42 and the tensioner portion 14. Additionally, the rectangular cross section of the tensioner cap slot 34 is shown. The tensioner portion 14 is hollow to allow for the tube 36 to rotate. The tensioner slot 34 guides the IM tube 36 to only move in one direction. The rod tube 36 is received between the intracondylar guides 26.

Figure 8:
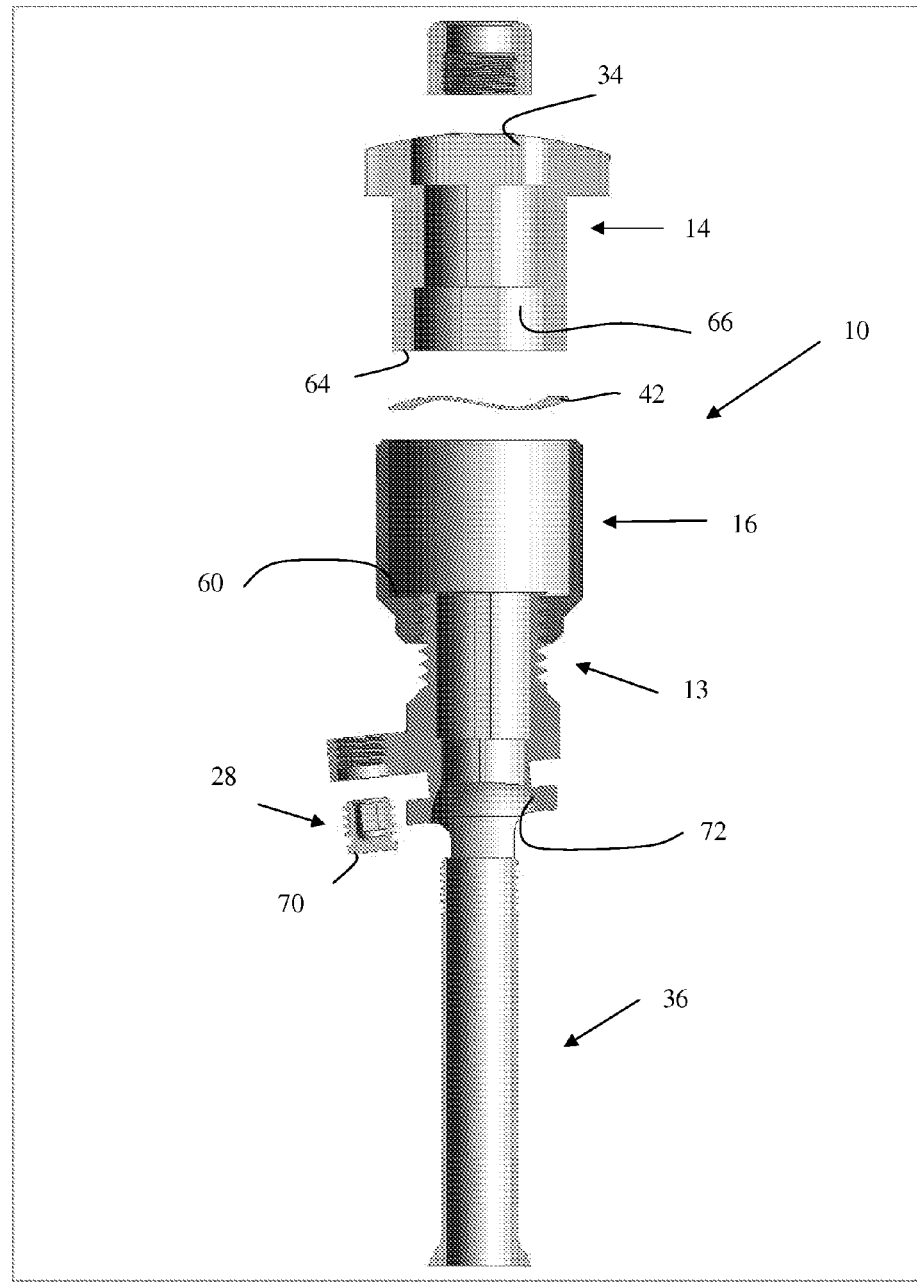
FIG. 8 is a cutaway of the exploded view of FIG. 6.

Turning now to FIG. 8, FIG. 8 is a cutaway of the exploded view of FIG. 6. The wave spring 42 rests between a locking portion abutting surface 60 and a tensioner portion abutting surface 64. The tensioner portion 14 includes a threaded frame portion recess 66 configured to receive the threaded portion of the frame when the locking portion 16 is rotated and translates along the axis of the frame 18.

A flat 70 on the set screw 28 retains the set screw within the frame 18. The flat also creates the interference fit between the frame 18 and the distal cutting block assembly. The flat is oriented at the angle of the slots 24 so that the entire flat surface 70 contacts the block assembly.

A spherical recess 72 on the frame 18 receives the IM rod 36. The spherical recess 72 is the surface which allows for rotation of the IM rod 36. The center of rotation of the IM rod is the center of the spherical recess 72, which is generally below the collet 10.

Figure 9:
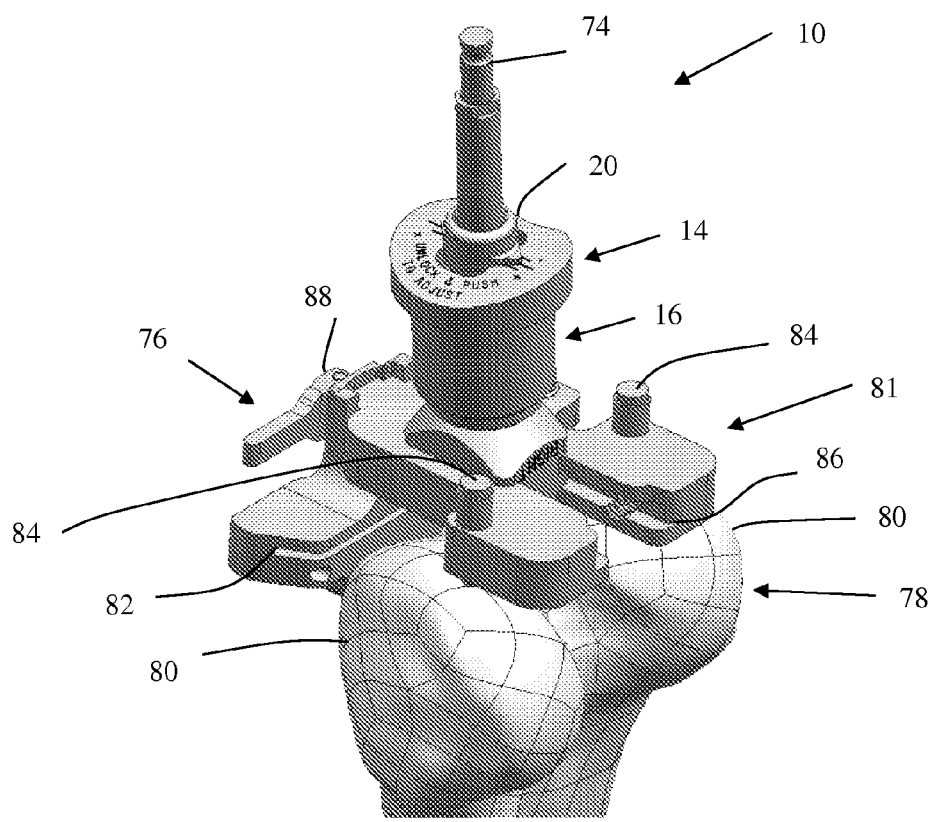
FIG. 9 is a variable collet attached to an IM rod and a femur.

Turning now to FIG. 9, FIG. 9 is a variable collet attached to an IM rod 74 and a femur 78. A distal cutting block assembly 76 is attached to the collet 10. In this embodiment, the distal cutting block assembly 76 is a cutting block for a primary total knee arthroplasty (TKA). However, other distal blocks, for example a revision or a unicompartmental cutting block, may alternatively be used depending on the type of surgical procedure being performed. The TKA cutting block 76 align along condyles 80 of the femur 78.

The cutting block assembly 76 may include a valgus alignment guide 81 and a distal cutting guide 82. The valgus alignment guide 81 includes floating spikes 84 and collet receiving slots 86. A cam 88 connects the distal cutting guide 82 to the valgus alignment guide 81. The cam 88 may be a thumb knob retaining member or any other connector to attach the distal cutting guide 82 to the valgus alignment guide 81. The floating spikes 84 may couple the valgus alignment guide 81 to the condyles 80 of the femur 78.

The collet 10 is placed over the IM rod 74 and lowered to the femur 80. The valgus alignment guide 81 is slid into the collet 10. The collet receiving slots 86 are slidably received along the receiving slots of the collet 10. The distal cutting guide 82 is attached perpendicularly to the valgus alignment guide 81. The cam 88 fixes the distal cutting guide 82 to the valgus alignment guide 81.

Figure 10:
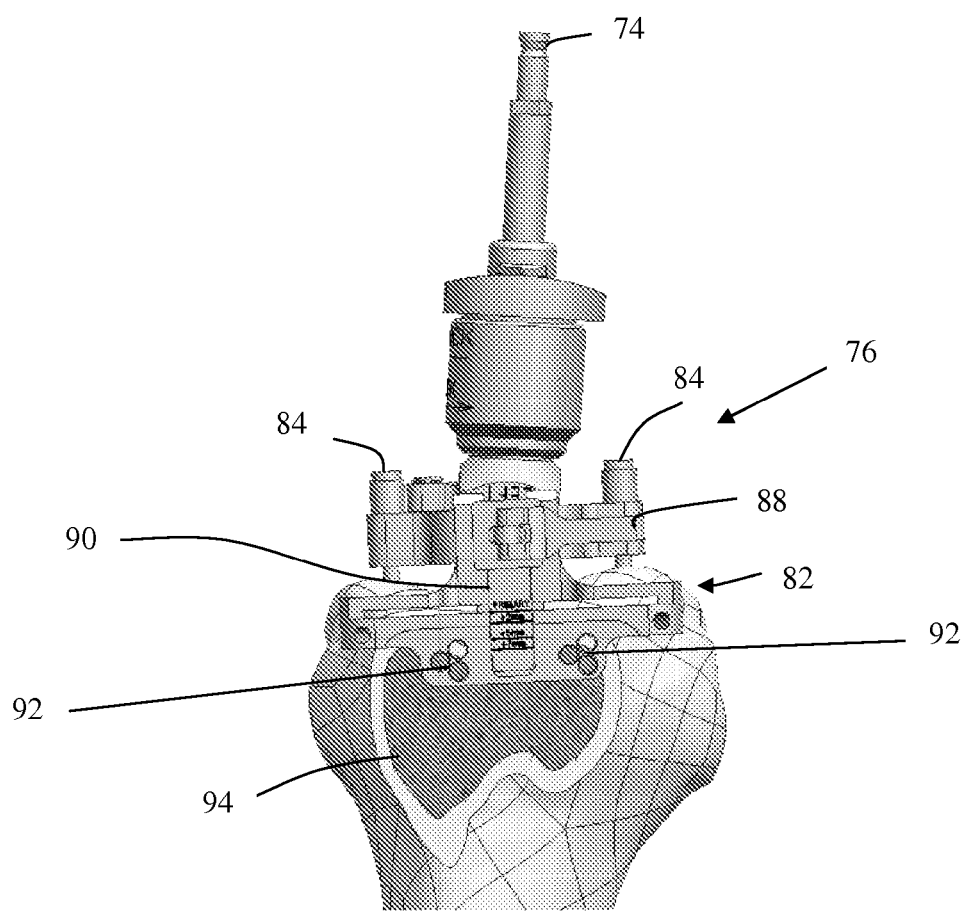
FIG. 10 is a variable collet attached to a femur.

Turning now to FIG. 10, FIG. 10 is a variable collet 10 attached to a femur 78. The femur 78 has already been prepared with an anterior resection 94. The distal cutting guide 82 may further include a depth gage 90 and spike holes 92. The depth gage 90 sets the depth of the distal cutting guide 82. The cam 88 fixes the depth of the cutting guide 82. When the depth is set, the surgeon may use spikes to fix the distal cutting guide 82 to the femur 78. The IM rod 74 and the collet 10 may then be removed before the distal cut is made. If additional depth is needed, then the depth of the distal cutting guide 82 may be adjusted by using the same holes in the femur, but using the adjacent spike holes 92. The distal cutting plane is then defined by the slot within the distal cutting guide 82.

The center of rotation of the collet 10 is approximately aligned with the cutting slot of the distal cutting guide 82.

Figure 11:
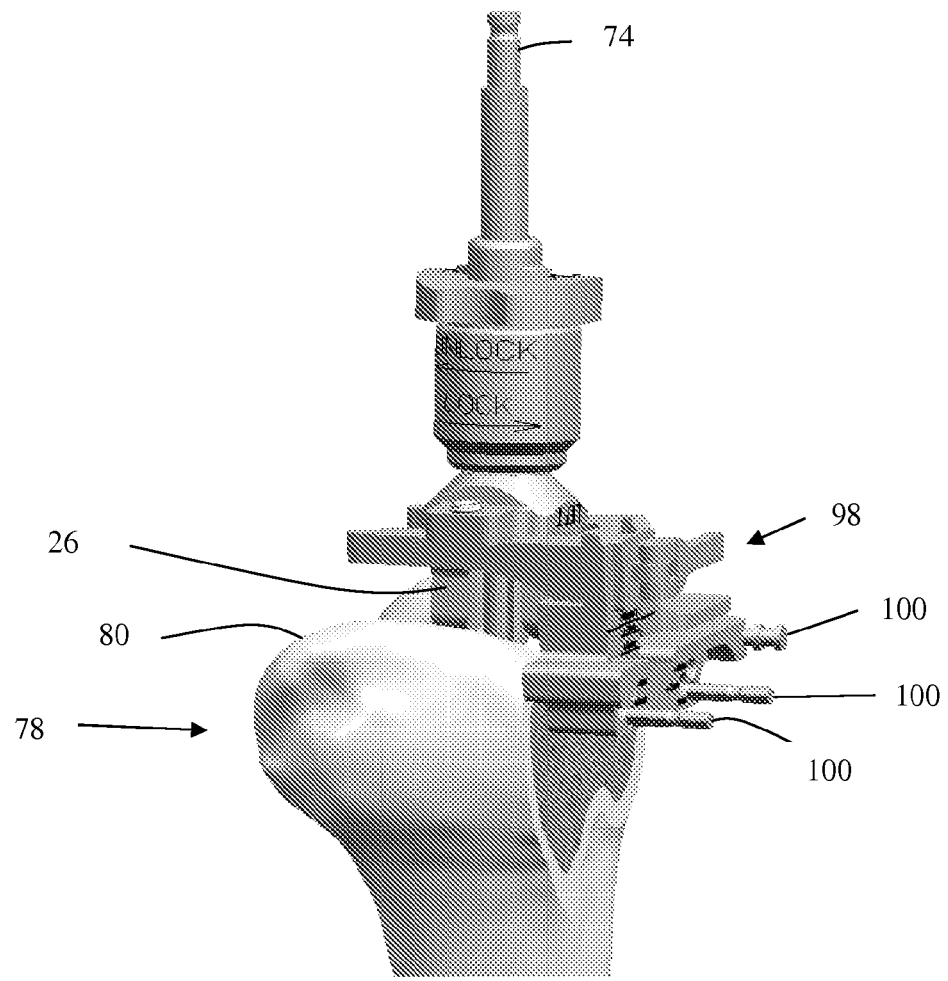
FIG. 11 is a variable collet attached to a unicondylar cutting guide.

Turning now to FIG. 11, FIG. 11 is a variable collet 10 attached to a unicondylar distal cutting guide 98. Spikes 100 fix the cutting guide 98 to the bone. The slot for making the distal cut for a unicondylar distal cutting guide 98 is positioned for cutting a single condyle 80 of the femur 78.

Figure 12:
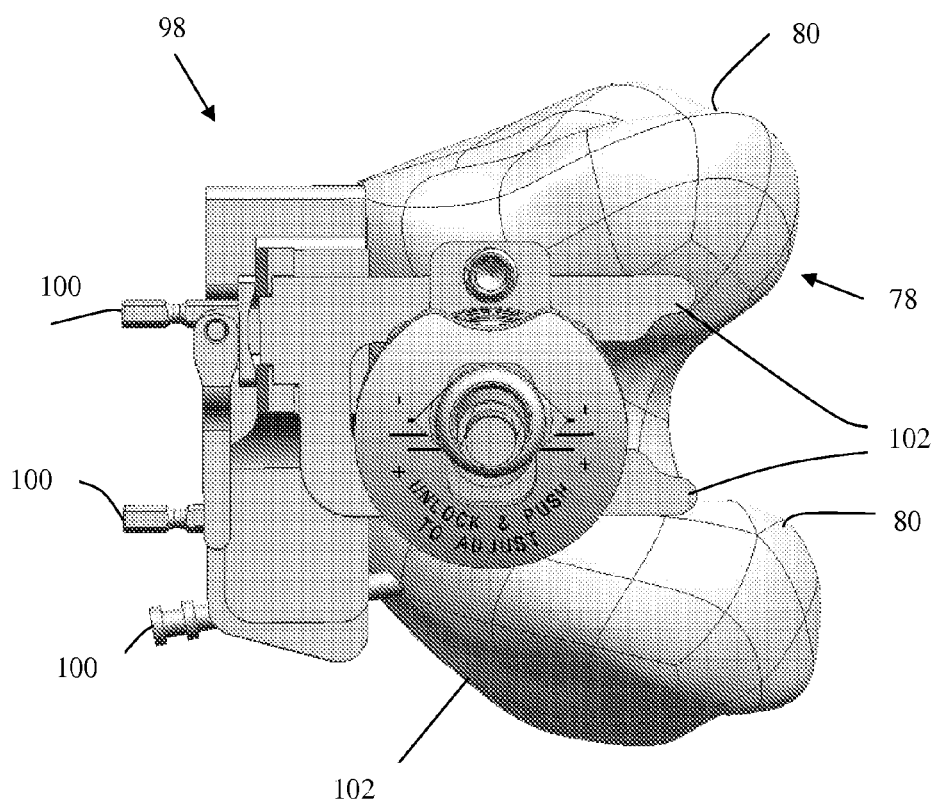
FIG. 12 is a distal view of a variable collet.

Turning now to FIG. 12, FIG. 12 is a distal view of a variable collet 10. A valgus alignment guide 102 may not have floating spikes as in previous embodiments. The valgus alignment guide 102 still aligns within the slots of the collet 10. Additionally, spikes 100 may have grooves which allow for extraction of the spikes from the guide 98.

In surgery, the surgeon first places the IM rod in the intramedullary canal. The variable collet, valgus alignment guide and distal cutting block are assembled and attached to the IM Rod. Then the valgus angle is adjusted as necessary. In one embodiment, when an anterior cut is already made, the adjustment aligns the lateral side of the distal cutting block either equal to or slightly proximal to the transition point. The transition point is the most distal point of the anterior cut on the lateral side. The variable collet is adjusted by first loosening the locking portion and then by pushing down on the tensioner portion to adjust to a different angle.

Next, the depth of the distal cutting guide is set. In one embodiment, the depth may be determined by using shims Femoral shims (for example, −2, 0 or +2 mm), assess the amount of distal resection. The 0 mm shim represents 9 mm of distal resection, which is equal to the thickness of the femoral implant. If this is chosen, this will be a measured resection. If necessary, more or less distal bone may be resected to account for flexion/extension stability.

Once the angle and the depth are set, then pins or spikes may be used to fix the cutting block to the femur. The variable collet, valgus alignment guide and IM rod may be removed for better visibility. The distal portion of the condyle or condyles may then be resected. The pins may then be removed and the guide removed from the femur.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of placing a cutting slot relative to a distal portion of a femur, comprising:
    driving an intramedullary rod in the intramedullary canal of the femur, the intramedullary rod having a longitudinal axis;
    positioning a slot over an anterior portion of the femur;
    attaching a guide to the intramedullary rod;
    attaching the slot to the guide wherein the guide is angularly adjustable with respect to the intramedullary rod such that adjusting the guide adjusts the varus/valgus angle of the slot;
    biasing the guide in tension by applying a spring force generally along the axis of the intramedullary rod; and
    locking the guide such that the slot is fixed relative to the intramedullary rod.

2. The method of claim 1, further comprising the step of adjusting the depth of the slot relative to the femur.

3. The method of claim 2, further comprising the step of fixing the slot to the guide.

4. The method of claim 1, wherein the slot guides a unicondylar distal cutting tool.

5. The method of claim 1 wherein the guide is fixed at an angle other than a perpendicular angle to the intramedullary rod thereby aligning the slot at a nonperpendicular angle to the anatomical axis of the femur.

6. The method of claim 1, further comprising the step of indicating the varus/valgus angle of the guide.

7. The method of claim 1, further comprising the step of resecting bone.

8. The method of claim 1, further comprising the step of implanting a portion of a knee prosthetic.

9. The method of claim 1, wherein the step of attaching a guide to the intramedullary rod includes the steps of attaching the guide to a variable collet and attaching the variable collet to the intramedullary rod.

10. The method of claim 1, wherein a variable collet allows the guide to be angularly adjustable.

* * * * *